United States Patent [19]
Jäger et al.

[11] Patent Number: 6,096,313
[45] Date of Patent: Aug. 1, 2000

[54] COMPOSITIONS CONTAINING IMMUNOGENIC MOLECULES AND GRANULOCYTE-MACROPHAGE COLONY STIMULATING FACTOR, AS AN ADJUVANT

[75] Inventors: Elke Jäger; Alexander Knuth, both of Frankfurt am Main, Germany

[73] Assignee: Ludwig Institute for Cancer Research, New York, N.Y.

[21] Appl. No.: 08/598,909

[22] Filed: Feb. 9, 1996

[51] Int. Cl.[7] .......................... A61K 39/00; A61K 39/38; A61K 38/00; C07K 1/00
[52] U.S. Cl. ..................................... 424/184.1; 424/185.1; 424/277.1; 435/975; 530/300; 530/328; 530/350
[58] Field of Search .............................. 424/185.1, 184.1, 424/277.1; 514/2, 21; 435/975; 530/300, 328, 350

[56] References Cited

U.S. PATENT DOCUMENTS 5,478,556  12/1995  Elliott et al. .
5,976,546  11/1999  Laus et al. .

FOREIGN PATENT DOCUMENTS 9421126  9/1994  WIPO .
9523234  8/1995  WIPO .

OTHER PUBLICATIONS

Dranoff et al., "Vaccination With Irradiated Tumor Cells–Engineered to Secrete Murine Granulocyte–Macrophage Colony Stimulating Factor Stimulates Potent, Specific, And Long Lasting Anti–Tumor Immunity", Proc. Natl. Acad. Sci. USA 90: –3539–3543 (Apr. 1993).

Cellular & Molecular Immunology, Abbas et al Editor, W. B. Saunder Comp. Philadelphia, 1991 pp. 245–248.

Wiltrout et al (Seminars in Oncology vol. 22(1) pp. 9–16), Feb. 1995.

Richard et al (Bone Marrow Transplantation vol. 11, No. 6, Jun. 1993 pp. 473–478).

Martin et al (Hepatology Oct. 1993 18(4) pp. 775–780).

Kawakami et al (PNAS USA vol. 91 pp. 3515–3519 Apr. 1994).

Perkins et al (American Journal of Hematology Aug. 1993 43(4) pp. 279–285).

Lazar et al (Molecular & Cellular Biology vol. 8 No. 3, Mar. 1988 pp. 1247–1252).

Burgess et al (Journal of Cell Biology vol. III, Nov. 1990 pp. 2129–2138).

Salgaller et al (Cancer Immunol. Immunother. vol. 39, 1994 pp. 105–116).

*Primary Examiner*—Albert Navarro
*Attorney, Agent, or Firm*—Fulbright & Jaworski, LLP

[57] ABSTRACT

Granulocyte-macrophage colony stimulating factor ("GM-CSF") has been found to act as an adjuvant when administered to subjects. Compositions of GM-CSF and immunogenic compositions are presented, as is the use of GM-CSF alone and in these compositions.

18 Claims, 3 Drawing Sheets

FIG. 1B

COMPOSITIONS CONTAINING IMMUNOGENIC MOLECULES AND GRANULOCYTE-MACROPHAGE COLONY STIMULATING FACTOR, AS AN ADJUVANT

FIELD OF THE INVENTION

This invention relates to compositions useful in the generation of immune responses especially the classes of molecules referred to as tumor rejection antigen precursors ("TRAPs") and tumor rejection antigens ("TRAs"). The immune response includes, inter alia, the production of antibodies against the TRAPs and TRAs, as well as T cells specific for complexes of TRA and major histocompatibility molecules ("MHCs"). Such T cells and antibodies may be generated, e.g., in a mouse, rat, rabbit, sheep, goat or other non-human animal, and then used in diagnostic methods to identify tumor presence. The compositions may also be used, therapeutically, via administration to a subject afflicted with a cancerous condition or one where cell transformation has taken place, such as melanoma or dysplastic nevi, to provoke an immune response against tumors, cancer cells, and transformed cells.

BACKGROUND AND PRIOR ART

The study of the recognition or lack of recognition of cancer cells by a host organism has proceeded in many different directions. Understanding of the field presumes some understanding of both basic immunology and oncology.

Early research on mouse tumors revealed that these displayed molecules which led to rejection of tumor cells when transplanted into syngeneic animals. These molecules are "recognized" by T-cells in the recipient animal, and provoke a cytolytic T-cell response with lysis of the transplanted cells. This evidence was first obtained with tumors induced in vitro by chemical carcinogens, such as methylcholanthrene. The antigens expressed by the tumors and which elicited the T-cell response were found to be different for each tumor. See Prehn, et al., J. Natl. Canc. Inst. 18: 769–778 (1957); Klein et al., Cancer Res. 20: 1561–1572 (1960); Gross, Cancer Res. 3: 326–333 (1943), Basombrio, Cancer Res. 30: 2458–2462 (1970) for general teachings on inducing tumors with chemical carcinogens and differences in cell surface antigens. This class of antigens has come to be known as "tumor specific transplantation antigens" or "TSTAs". Following the observation of the presentation of such antigens when induced by chemical carcinogens, similar results were obtained when tumors were induced in vitro via ultraviolet radiation. See Kripke, J. Natl. Canc. Inst. 53: 333–1336 (1974).

While T-cell mediated immune responses were observed for the types of tumor described supra, spontaneous tumors were thought to be generally non-immunogenic. These were therefore believed not to present antigens which provoked a response to the tumor in the tumor carrying subject. See Hewitt, et al., Brit. J. Cancer 33: 241–259 (1976).

The family of tum⁻ antigen presenting cell lines are immunogenic variants obtained by mutagenesis of mouse tumor cells or cell lines, as described by Boon et al., J. Exp. Med. 152: 1184–1193 (1980), the disclosure of which is incorporated by reference. To elaborate, tum⁻ antigens are obtained by mutating tumor cells which do not generate an immune response in syngeneic mice and will form tumors (i.e., "tum⁺" cells). When these tum⁺ cells are mutagenized, they are rejected by syngeneic mice, and fail to form tumors (thus "tum⁻"). See Boon et al., Proc. Natl. Acad. Sci. USA 74: 272 (1977), the disclosure of which is incorporated by reference. Many tumor types have been shown to exhibit this phenomenon. See, e.g., Frost et al., Cancer Res. 43: 125 (1983).

It appears that tum⁻ variants fail to form progressive tumors because they elicit an immune rejection process. The evidence in favor of this hypothesis includes the ability of "tum⁻" variants of tumors, i.e., those which do not normally form tumors, to do so in mice with immune systems suppressed by sublethal irradiation, Van Pel et al., Proc. Natl, Acad. Sci. USA 76: 5282–5285 (1979); and the observation that intraperitoneally injected tum⁻ cells of mastocytoma P815 multiply exponentially for 12–15 days, and then are eliminated in only a few days in the midst of an influx of lymphocytes and macrophages (Uyttenhove et al., J. Exp. Med. 152: 1175–1183 (1980)). Further evidence includes the observation that mice acquire an immune memory which permits them to resist subsequent challenge to the same tum⁻ variant, even when immunosuppressive amounts of radiation are administered with the following challenge of cells (Boon et al., Proc. Natl, Acad. Sci. USA 74: 272–275 (1977); Van Pel et al., supra; Uyttenhove et al., supra). Later research found that when spontaneous tumors were subjected to mutagenesis, immunogenic variants were produced which did generate a response. Indeed, these variants were able to elicit an immune protective response against the original tumor. See Van Pel et al., J. Exp. Med. 157: 1992–2001 (1983). Thus, it has been shown that it is possible to elicit presentation of a so-called "tumor rejection antigen" in a tumor which is a target for a syngeneic rejection response. Similar results have been obtained when foreign genes have been transfected into spontaneous tumors. See Fearson et al., Cancer Res. 48: 2975–1980 (1988) in this regard.

A class of antigens has been recognized which are presented on the surface of tumor cells and are recognized by cytotoxic T cells, leading to lysis. This class of antigens will be referred to as "tumor rejection antigens" or "TRAs" hereafter. TRAs may or may not elicit antibody responses. The extent to which these antigens have been studied, has been via cytolytic T cell characterization studies in vitro i.e., the study of the identification of the antigen by a particular cytolytic T cell ("CTL" hereafter) subset. The subset proliferates upon recognition of the presented tumor rejection antigen, and the cells presenting the antigen are lysed. Characterization studies have identified CTL clones which specifically lyse cells expressing the antigens. Examples of this work may be found in Levy et al., Adv. Cancer Res. 24: 1–59 (1977); Boon et al., J. Exp. Med. 152: 1184–1193 (1980); Brunner et al., J. Immunol. 124: 1627–1634 (1980); Maryanski et al., Eur. J. Immunol. 124: 1627–1634 (1980); Maryanski et al., Eur. J. Immunol. 12: 406–412 (1982); Palladino et al., Canc. Res. 47: 5074–5079 (1987). This type of analysis is required for other types of antigens recognized by CTLs, including major histocompatibility antigens, the male specific H-Y antigens, and a class of antigens, referred to as "tum⁻" antigens, and discussed herein.

A tumor exemplary of the subject matter described supra is known as P815. See DePlaen et al., Proc. Natl. Acad. Sci. USA 85: 2274–2278 (1988); Szikora et al., EMBO J 9: 1041–1050 (1990), and Sibille et al., J. Exp. Med. 172: 35–45 (1990), the disclosures of which are incorporated by reference. The P815 tumor is a mastocytoma, induced in a DBA/2 mouse with methylcholanthrene and cultured as both an in vitro tumor and a cell line. The P815 line has generated many tum⁻ variants following mutagenesis, including variants referred to as P91A (DePlaen, supra), 35B (Szikora, supra), and P198 (Sibille, supra). In contrast to tumor rejection antigens—and this is a key distinction—the tum⁻ antigens are only present after the tumor cells are mutagenized. Tumor rejection antigens are present on cells of a given tumor without mutagenesis. Hence, with reference to the literature, a cell line can be tum⁺, such as the line referred to as "P1", and can be provoked to produce tum⁻ variants. Since the tum⁻ phenotype differs from that of the parent cell line, one expects a difference in the DNA of tum⁻ cell lines as compared to their tum⁺ parental lines, and this difference can be exploited to locate the gene of interest in tum⁻ cells. As a result, it was found that genes of turn variants such as P91A, 35B and P198 differ from their normal alleles by point mutations in the coding regions of the gene. See Szikora and Sibille, supra, and Lurquin et al., Cell 58: 293–303 (1989). This has proved not to be the case with the TRAs of this invention. These papers also demonstrated that peptides derived from the tum⁻ antigen are presented by the $L^d$ molecule for recognition by CTLs. P91A is presented by $L^d$, P35 by $D^d$ and P198 by $K^d$.

Prior patent application PCT/US92/04354, and U.S. Pat. No. 5,342,774, both of which are incorporated by reference describe inventions involving, inter alia, genes and other nucleic acid molecules which code for various TRAPs, which are in turn processed to tumor rejection antigen, or "TRAs". SEQ ID NOS: 1–26 which are a part of the subject PCT application, present sequences of genes coding for various TRAPs, and the TRA referred to hereafter as MZ2-E, which is derived from MAGE-1 TRAP (SEQ ID NO: 26).

The genes are useful as a source for the isolated and purified tumor rejection antigen precursor and the TRA themselves, either of which can be used as an agent for treating the cancer for which the antigen is a "marker", as well as in various diagnostic and surveillance approaches to oncology, discussed infra. It is known, for example, that tum⁻ cells can be used to generate CTLs which lyse cells presenting different tum⁻ antigens as well as tum⁺ cells. See, e.g., Maryanski et al., Eur. J. Immunol 12: 401 (1982); and Van den Eynde et al., Modern Trends in Leukemia IX (June 1990), the disclosures of which are incorporated by reference. The tumor rejection antigen precursor may be expressed in cells transfected by the gene, and then used to generate an immune response against a tumor of interest.

In the parallel case of human neoplasms, it has been observed that autologous mixed lymphocyte-tumor cell cultures ("MLTC" hereafter) frequently generate responder lymphocytes which lyse autologous tumor cells and do not lyse natural killer targets, autologous EBV-transformed B cells, or autologous fibroblasts (see Anichini et al., Immunol. Today 8: 385–389 (1987)). This response has been particularly well studied for melanomas, and MLTC have been carried out either with peripheral blood cells or with tumor infiltrating lymphocytes. Examples of the literature in this area including Knuth et al., Proc. Natl. Acad. Sci. USA 86: 2804–2802 (1984); Mukherji et al., J. Exp. Med. 158: 240 (1983); Hérin et all, Int. J. Canc. 39: 390–396 (1987); Topalian et al, J. Clin. Oncol 6: 839–853 (1988). Stable cytolytic T cell clones have been derived from MLTC responder cells, and these clones are specific for the tumor cells. See Mukherji et al., supra, Hérin et all, supra, Knuth et al., supra. The antigens recognized on tumor cells by these autologous CTLs do not appear to represent a cultural artifact, since they are found on tumor cells in vivo. Topalian et al., supra; Degiovanni et al., Eur. J. Immunol. 20: 1865–1868 (1990). These observations, coupled with the techniques used herein to isolate the genes for specific murine tumor rejection antigen precursors, have led to the isolation of nucleic acid sequences coding for tumor rejection antigen precursors of TRAs presented on human tumors. It is now possible to isolate the nucleic acid sequences which code for tumor rejection antigen precursors, including, but not being limited to those most characteristic of a particular tumor, with ramifications that are described infra.

Additional work has focused upon the presentation of TRAs by the class of molecules known as major histocompatibility complexes, or "MHCs". Human forms of these molecules are "human leukocyte antigens" or "HLAs". This work has resulted in several unexpected discoveries regarding the field. Specifically, U.S. Pat. Nos. 5,405,940 and 5,462,871, the disclosures of which is incorporated by reference, nonapeptides are taught which are presented by HLA-A1 molecules. The reference teaches that given the known specificity of particular peptides for particular HLA molecules, one should expect particular peptides to bind one HLA molecule. These peptides are also presented in Traversari et al., J. Exp. Med. 176: 1453–1457 (1992). This is important, because different individuals possess different HLA phenotypes. As a result, while identification of particular peptides or of particular motifs, and the peptides which are members thereof, as being partners for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

In U.S. patent application Ser. No. 08/008,446, filed Jan. 22, 1993, now abandoned and incorporated by reference, the fact that the MAGE-1 expression product is processed to a second TRA is disclosed. This second TRA is presented by HLA-Cw* 1601 molecules. The disclosure shows that a given TRAP can yield a plurality of TRAs.

In U.S. Pat. No. 5,487,974 and incorporated by reference herein, tyrosinase is described as a tumor rejection antigen precursor. This is a well known molecule as per Kwon, U.S. Pat. No. 4,898,814. This reference discloses that a molecule which is produced by some normal cells (e.g., melanocytes), is processed in tumor cells to yield a tumor rejection antigen that is presented by HLA-A2 molecules. The peptide presented thereby is described in U.S. Application Ser. No. 08/057,714, filed Apr. 28, 1993, now abandoned also incorporated by reference. Additional tyrosinase derived peptides presented by HLA molecules are set forth in Ser. No. 08/203,054, now U.S. Pat. No. 5,530,096 and Ser. No. 08/233,305 now U.S. Pat. No. 5,519,117 filed Feb. 28, 1994 and Apr. 26, 1994 and are incorporated by reference.

Other peptides which are TRAs are described in additional patent applications. U.S. patent application Ser. No. 08/195,186, now U.S. Pat. No. 5,558,995 filed Feb. 14, 1994, and incorporated by reference herein, sets forth three peptides, which are derived from MAGE-1 and which complex with HLA-Cw* 1601. Ser. No. 08/196,630, now abandoned filed Feb. 15, 1994, discloses an unrelated tumor rejection antigen precursor, the so-called "BAGE" gene, and peptides derived therefrom, which are processed and then presented by HLA-Cw* 1601. Additional coding sequences for a tumor rejection antigen precursor referred to as Melan-A are set forth in Ser. No. 08/032,978, now U.S. Pat. No. 5,620,886 filed Mar. 18, 1993 and incorporated by reference. A more extended sequence for this gene is set forth in Ser. No. 08/272,351, now abandoned filed Jul. 8, 1994 incorporated by reference. In Ser. No. 08/96,039, filed Jul. 22, 1993, now abandoned the sequence of tumor rejection antigen precursor GAGE is set forth, and is incorporated by reference.

A series of peptides which provoke lysis by cytolytic T cells when presented by MHC molecules are set forth in Ser. No. 08/217,186, now U.S. Pat. No. 5,585,461 Ser. No. 08/217,188, now U.S. Pat. No. 5,554,724 and Ser. No. 08/217,187, now U.S. Pat. No. 5,554,506 all filed on Mar. 24, 1994, and all of which are incorporated by reference herein. The first of these applications discloses MAGE-3 derived peptides presented by HLA-A2. Five peptides are of interest. The second application presents 11 sequences derived from MAGE-2, believed to complex with HLA-A2.1 molecules. The last of these applications discloses two additional peptides derived from MAGE-3 which complex to HLA-A2. Ser. No. 08/190,411, now U.S. Pat. No. 5,541,104 filed Apr. 1, 1994 and incorporated by reference, sets forth three peptides derived from MAGE-1, which are immunogenic in that they provoke production of antibodies in a host animal to which they have been administered. Ser. No. 08/253,503, now U.S. Pat. No. 5,589,334 filed Jun. 3, 1994 and incorporated by reference, teaches a further tumor rejection antigen precursor gene and a peptide, derived therefrom, which is presented by HLA-B44 molecules. Further in the application of Coulie, Ikeda and Boon-Falleur, Ser. No. 08/316,231 now U.S. Pat. No. 5,830,753 incorporated by references, a sequence coding for a tumor rejection antigen precursor known as DAGE is set forth. DAGE is found almost universally on tumor cells, and only on testis cells with respect to normal cell expression. This makes it especially useful for cancer diagnosis and in the applications disclosed herein. The above listing should not be presumed to be exhaustive of the TRAP and TRA literature, but is presented to show its diversity and the fact that these materials not only provoke T cell proliferation, but also stimulate production of antibodies. It is well known that antibody producing cells can be used as a source to produce hybridomas, which in turn produce monoclonal antibodies. Thus, when the term "antibodies" is used herein, it encompasses both polyclonal and monoclonal antibodies.

U.S. patent application Ser. No. 08/142,368 now U.S. Pat. No. 5,925,729, Ser. No. 08/190,411 now U.S. Pat. No. 5,541,104 and Ser. No. 08/315,961, now abandoned all incorporated by reference discuss the usefulness of combining TRAPs or TRAs with various materials as adjuvants, to produce vaccines, immunogenic compositions, etc. Adjuvants, broadly defined, are substances which promote immune responses. Frequently, the adjuvant of choice if Freund's complete adjuvant, or killed *B. pertussis* organisms, used in combination with alum precipitated antigen. A general discussion of adjuvants is provided in Goding, Monoclonal Antibodies: Principles & Practice (Second edition, 1986), at pages 61–63, which are incorporated by reference herein. Goding notes, however, that when the antigen of interest is of low molecular weight, or is poorly immunogenic, coupling to an immunogenic carrier is recommended. Such molecules, according to Godinq, generally have molecular weights below about 1000. Among the carriers suggested by Goding, at page 283, are keyhole limpet hemocyanin, bovine serum albumin, ovalbumin, and fowl immunoglobulin.

What is problematic about such carriers, however, is that frequently they are also immunogenic themselves. Thus, the immune response may be a general one, with part, most, or all of it being directed against the carrier molecule rather than the immunogen itself.

Exemplary of developments in the art as they relate to adjuvants is U.S. Pat. No. 5,057,540 to Kensil, et al, the disclosure of which is incorporated by reference herein. Kensil et al disclose the preparation of various saponin extracts, which are useful as adjuvants in immunogenic compositions. As natural products, the extracts are not completely defined. Kensil, et al do provide a complete and enabling disclosure for how various extracts, including QA-7, QA-19, and QA-21 (also referred to as QS-21) are prepared. Experiments are set forth in which bovine serum albumin ("BSA") was combined with various extracts (examples 8 and 9), and where feline leukemia virus recombinant glycoprotein "gp7ORΔ was tested, following absorption to aluminum hydroxide (alum). The two immunogens tested, however, are expected to be immunogenic in their own right (gp7ORΔ has a molecular weight of 70 kd, and serum albumin has about the same molecular weight). No experiments were carried out at all on molecules which should, per se, be considered to be poorly or even non-immunogenic, and thus would be expected to require the use of alum absorption or the use of haptenic carriers for provocation of a response.

In PCT Application WO9219758, which corresponds to defensive publication 7697275, which is incorporated by reference herein, an adjuvant referred to as "MTP-MF59" is disclosed. This adjuvant is used in connection with a *Plasmodium falciparum* protein, "Pfs-25-B". This combination is described as a transmission blocking vaccine. The *P. falciparum* protein is itself large enough to be immunogenic. Thus, none of the art shows that the improved adjuvants can be used in combination with presumptively non-immunogenic proteins and peptides to yield immunologically effective compositions. This is especially true for TRAP and TRA molecules, as outlined supra.

Granulocyte-macrophage colony stimulating factor ("GM-CSF" hereafter), is a well known cytokine, having a molecular weight of about 18–32 kDA on SDS-PAGE, or 30 kDA by gel filtration. It contains 127 amino acids. Other properties of the molecule are summarized in, e.g. Crosier et al., "Granulocyte-Macrophage Colony Stimulating Factor" in Aggarwal, et al., Human Cytokines: Handbook For Basic And Clinical Research (Blackwell Scientific Publications, 1992), chapter 14 in particular, the disclosure of which is incorporated by reference. The patent literature on GM-CSF is vast. Exemplary of this literature are U.S. Pat. Nos. 5,437,994; 5,211,947; 5,199,942; 5,198,417; 5,178,855; and 5,162,111, all of which are incorporated by reference. These patents disclose various uses of GM-CSF in the area of treatment of particular diseases and pathologies, where expansion of the granulocyte and/or macrophage population of the recipient is desirable or necessary. None of these references is desirable or necessary. None of these references teach the use of GM-CSF as an adjuvant, in the sense provided by the preceding example. It has now been found that GM-CSF does possess properties which permit it to be used as an adjuvant to improve, enhance, or provoke an immune response against a particular immunogen. This is the subject of the invention, described in greater detail infra.

DETAILED DESCRIPTION OF PREFERRED EMBODIMENTS

EXAMPLE 1

This example is intended as background information for the further experiments which follow.

In these experiments, all patients are afflicted with either stage IV or high risk stage III malignant melanoma. In the case of stage IV melanoma, patients have a median survival of one year, and only a 15% chance of long term survival. See Balch, et al., *Cutaneous Melanoma* (J. B. Lippincott, Philadelphia, 1992). In the case of high risk stage III melanoma, patients have a median survival of 1–2 years, and a 9% chance of long term survival. Balch, supra. It will be clear that new approaches to the treatment of such patients are needed.

The patient pool was restricted to patients who have recovered fully from any surgery. Further, the patients must not have received any chemotherapy or immunotherapy within the four weeks precedent to treatment, and must not have received nitrosourea drugs for six weeks precedent. They must also have an expected survival of at least three months, a Karnofsky performance status of 60% or more, and laboratory results as follows:

Granulocytes>2,500/ul

Lymphocytes>700/ul

Platelets>100,000/ul

Serum creatinine>2 mg/dl

Serum bilirubin>2 mg/dl

The patients must test positive for HLA-A2 expression, the Melan A gene, and gp 100 both of which are molecules, expression of which is associated with melanoma. The testing for expression of these molecules was done by PCR or antibody assays, using well known methodologies not discussed here. The patients must be over 18 years old, and competent to give written consent.

Patients were excluded if they showed clinically significant heart disease (NYHA Class III or IV), any other serious illnesses, such as active infections requiring antibiotics or bleeding disorders, if they were receiving antihistamines, non-steriodal anti-inflammatory drugs, or corticosteroids. Patients were also excluded if they suffered from immunodeficiency, previous splenectomy, or radiation therapy on the spleen. Further, patients wee excluded if they were pregnant, lactating, or were of childbearing age (unless adequate methods of contraception were used). Finally, if metastatic disease of the central nervous system was present, the patient was excluded.

As part of the treatment protocol the patients were all treated as outpatients, and received a complete, pretreatment physical examination including an eye examination. A complete neurological and dermatological status exam, for vitiligo, was required.

Five patients referred to as NW28, NW29, NW30, NW33 and NW37 who qualified for the protocol received injections of the following peptides:

Tyr Met Asp Gly Thr Met Ser Gln Val (SEQ ID NO: 1)

Glu Ala Ala Gly Ile Gly Ile Leu Thr Val (SEQ ID NO: 2)

Tyr Leu Glu Pro Gly Pro Val Thr Ala (SEQ ID NO: 3)

Leu Leu Asp Gly Thr Ala Thr Leu Arg Leu (SEQ ID NO: 4)

Gly Ile Leu Gly Phe Val Phe Thr Leu (SEQ ID NO: 5)

Met Leu Leu Ala Val Leu Tyr Cys Leu (SEQ ID NO: 6)

Three of the five subjects (i.e., NW30, 33 and 37) received 100 ug injections of each of these six peptides into the anterior regions of the forearms and the thighs (injection site alternated for each injection in the protocol). The peptides were administered as 100 ug of the peptide combined in 0.3 ml of phosphate buffered saline (pH 7.4), for SEQ ID NO: 1, or 0.3 ml of PBS containing dimethyl sulphoxide, for SEQ ID NOS: 2–5, which are not water soluble. The peptide solutions contained DMSO at 5% concentration for SEQ ID NOS: 2 and 5, and 10% for SEQ ID NOS: 3 and 4.

The complete set of peptide injections were administered according to the schedule of Table 1, infra. Injections were made at separate sites, more than 10 cm apart. Peptides were not mixed in the injection.

The remaining two patients (i.e. NW28 and NW29) received peptides on a different schedule, as outlined in Table 2, infra. Specifically, the patients received 100 ug of each of the peptides weekly, for four weeks, followed by a four week break, receiving no injection. The pattern was then repeated three more times, for a total of four, 8 week blocks for patient NW29.

Patient NW28 followed this protocol but for six 4 week blocks.

EXAMPLE 2

As indicated, supra, example 1 may be regarded as the precursor to the experiments which are the heart of this invention.

Following completion of the protocols of Example 1, patients received systemic pretreatment with GM-CSF, at 75 µg per day, subcutaneously. Injection schedules are set forth in Tables 1 and 2, infra.

Three days after the initial administration of GM-CSF, the patients received intradermal injections of 100 ug of each of SEQ ID NOS: 1–5, as well as 100 ug of the peptide of SEQ ID NO: 6. The injections were made at different body sites. Delayed Type Hypersensitivity (DTH) reactions were measured 48 hours later. On day 8, a second round of peptide immunizations were carried out, and DTH reactions were measured 48 hours after that. Table 3, which follows, infra, shows the results of the DTH assays. In this table a "-" indicates no reaction, (+) denotes redness and induration of >4 mm in diameter, and "+"1 indicates redness of >8 mm diameter. A "++" indicates central necrosis.

A DTH reaction is defined as redness and palpable induration of the skin of at least 4 mm at the peptide injection site. It is assumed that the DTH reaction is the result of binding of an injected peptide to MHC Class I molecules (in this case, HLA-A2 molecules), on antigen presenting cells located in the skin, which in turn leads to peptide specific cellular reactions involving CD4$^+$ and CD8$^+$ T lymphocytes. DTH reactions were also tested in the patient pool prior to the administration of the GM-CSF.

Of the five patients, all showed a much more intense reaction to SEQ ID NO: 5 following GM-CSF pretreatment than without it. This was also true for SEQ ID NO: 6. For SEQ ID NO: 2, one of the patients showed a stronger DTH reaction after GM-CSF pretreatment than before.

There were also "de novo" DTH reactions observed. Some of the peptides provoked no, or an unobservable DTH reaction, without GM-CSF pretreatment, but did show such reactions after it. For SEQ ID NOS: 2, 3 of the 5 patients exhibited a reaction following GM-CSF pretreatment. For SEQ ID NO: 3, two of the five patients showed a response only after GM-CSF pretreatment, and two of five patients showed a response following pretreatment when SEQ ID NO: 1 was used.

EXAMPLE 3

It was also of interest to determine if the DTH response could be reactivated. To test this, the patients received peptide injections intradermally, following the protocol previously set forth, one week after the first DTH experiments were carried out. Three of the patients showed reactivation to the peptide of SEQ ID NO: 2, while 1 of 5 showed reactivation to SEQ ID NO: 5.

In this experiment, and all others, a control peptide which binds to HLA-A1 molecules was used. The patients were HLA-A1 negative. No DTH reaction was observed at any time.

EXAMPLE 4

Additional experiments were then carried out to study the nature of the cytolytic T cell responses of the subjects of the study.

Peptides, as set forth in Table 3, were used. Three of the patients described supra, i.e., NW28, NW29 and NW30, were tested. All had measurable metastatic disease. The patients were injected with 100 ug of each peptide (200 ul final volume), intradermally, at disease free sites at least 10 cm apart. Preferred sites for peptide injection were the periumbilical region, the front parts of the thigh, and the medial part of the forearms. Injections were repeated, weekly, four times. During the fourth immunization cycle, GM-CSF was injected (75 ug, subcutaneously), for daily injections. The GM-CSF injections began three days before peptide immunization, and continued until two days after injection.

In order to determine CTL response, samples of T2 cells ($10^6$ cells, per sample), were first incubated with 2 ug of mAb 2.1, which is known to stabilize empty MHC molecules. See Bodmer, et al., Nature 342: 443–446 (1989). The T2 cells were then labelled with 100 $\mu$Ci of Na($^{51}$Cr)O$_4$, washed once, and resuspended in serum free medium with 1 ug/ml of peptide. Cells were incubated for one hour at room temperature. These cells were then pulsed, with peptides, following well known techniques.

Responder cells were then added. These were peripheral blood lymphocytes (PBLs), taken from the subject, which had been removed, frozen until ready for use, and then thawed and washed in RPMI 1640, supplemented with 10% human serum, L-asparagine (50 mg/l), L-arginine (242 mg/l) and L-glutamine (300 Mg/l). The PBLS were seeded in 48 well plates ($1\times10^6$ cells/well), in 0.5 ml medium. Remaining PBLs, irradiated at 3000 rads, were resuspended in 1 ml serum free RPMI, supplemented with β2 microglobulin (2.5 ug/ml), and 10 ug/ml of peptide, and incubated for one hour at room temperature. Stimulating cells (i.e., peptide pulsed T2 cells), were resuspended and added to the MLTC at $1\times10^7$ cells/well, together with IL-2 (25 U/ml, final volume=1 ml/well). After seven days, responder cells were harvested, washed, and transferred to 24 well plates. Peptide was added at 1 ug/ml. At day 14, responder cells were harvested for the cytotoxicity assay, now explained.

The PBLS acted as responder cells, and were added to the peptide pulsed T2 cells ("target cells"), at effector/target ratios of 90, 30, 10, 3 and 1. Unlabelled K562 cells were added to the responder cells at a ratio of 80:1, to block NK activity. As a control, T2 cells not pulsed with peptides, were also used.

Mixtures of $^{51}$Cr labelled targets (1000 cells/well), and 50 ul of responder CTL suspensions were then incubated in conical 96 well microtiter plates for four hours in a water saturated atmosphere, with 5% CO$_2$, at 37° C. Plates were centrifuged at 2000×g, for five minutes, 100 ul of supernatant was removed, and free radioactivity measured in a γ-counter.

The percentage of specific $^{51}$Cr release was determined by the formula $$\frac{\text{Exp}(^{51}Cr \text{ release}) - \text{Spont}(^{51}Cr \text{ release})}{\text{MAX}(^{51}Cr \text{ release}) - \text{Spont}(^{51}Cr \text{ release})} \times 100\%$$

Maximum $^{51}$Cr release was obtained by adding 100 ul Nonidet P40 1% (Sigma) to labelled target cells. Spontaneous $^{51}$Cr release ranged from 5% to 10% of total counts incorporated into cells. The amount of $^{51}$Cr released from T2 cells unlabelled with peptide ranged from 3% to 10%. A CTL response was positive when peptide specific lytic activity exceeded 20% at an E:T ratio of 90:1.

In 2 of the 3 patients (NW28 and NW29), the intradermal inoculation of synthetic melanoma associated peptides alone did induce CTLs.

Figure 1A:
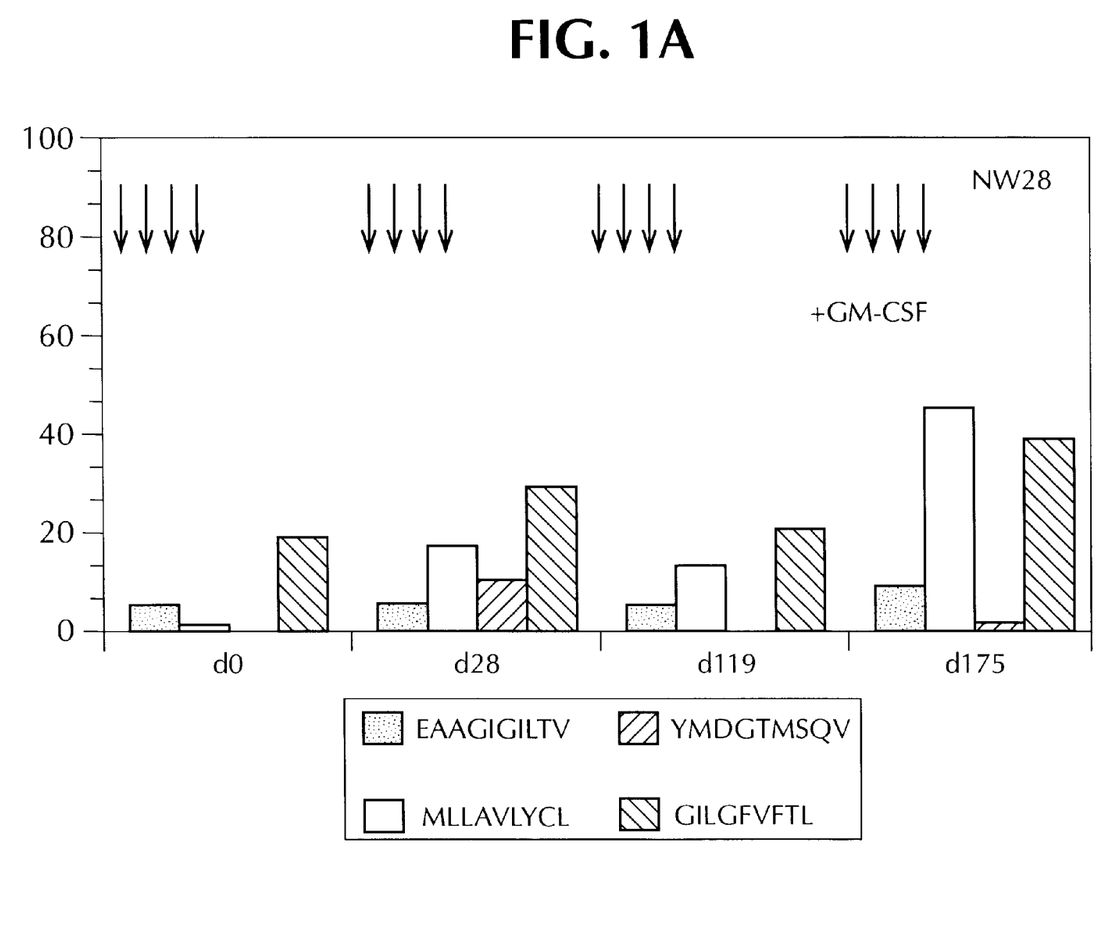
FIGS. 1A, 1B and 1C show, respectively, the induction of peptide specific CTLs in patients NW28, NW29, and NW30.
Figure 1B:
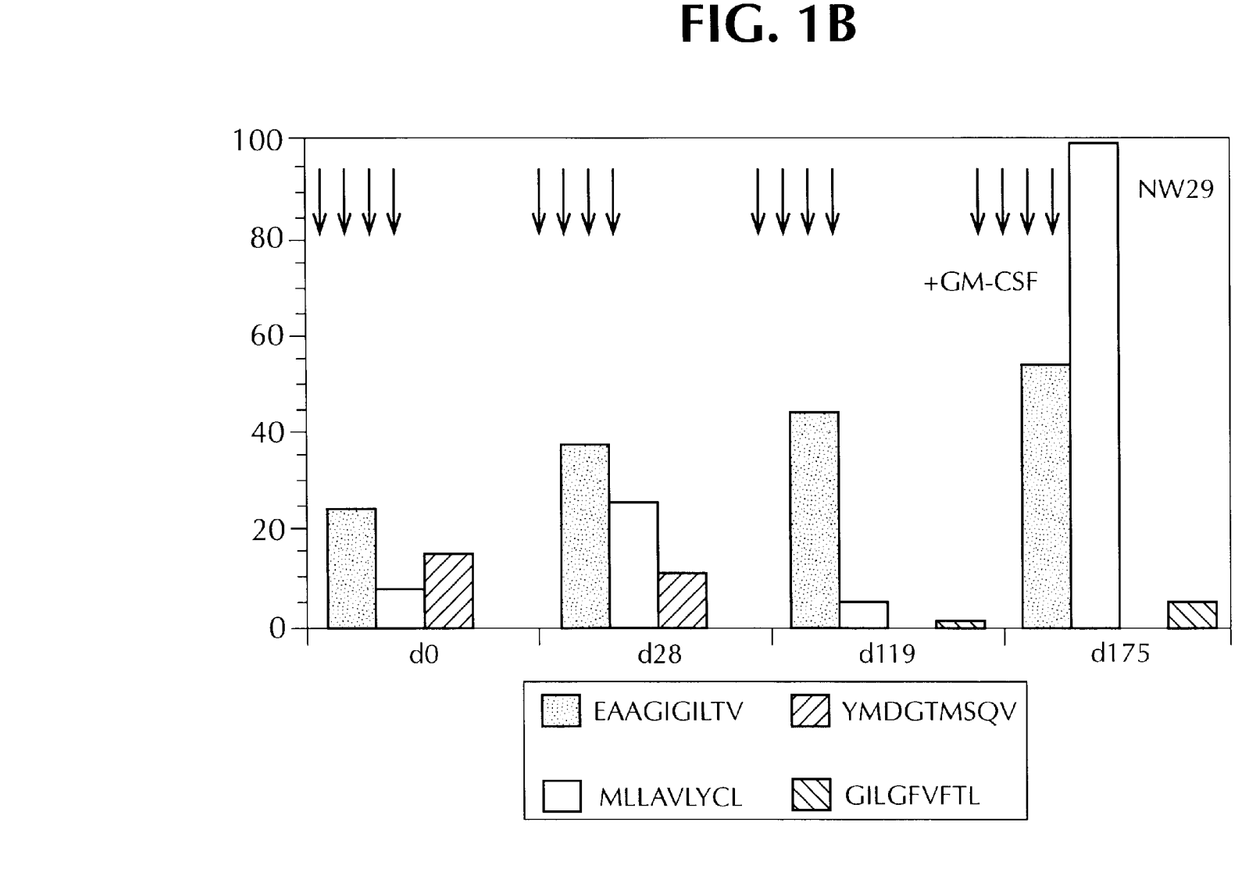
Figure 1C:
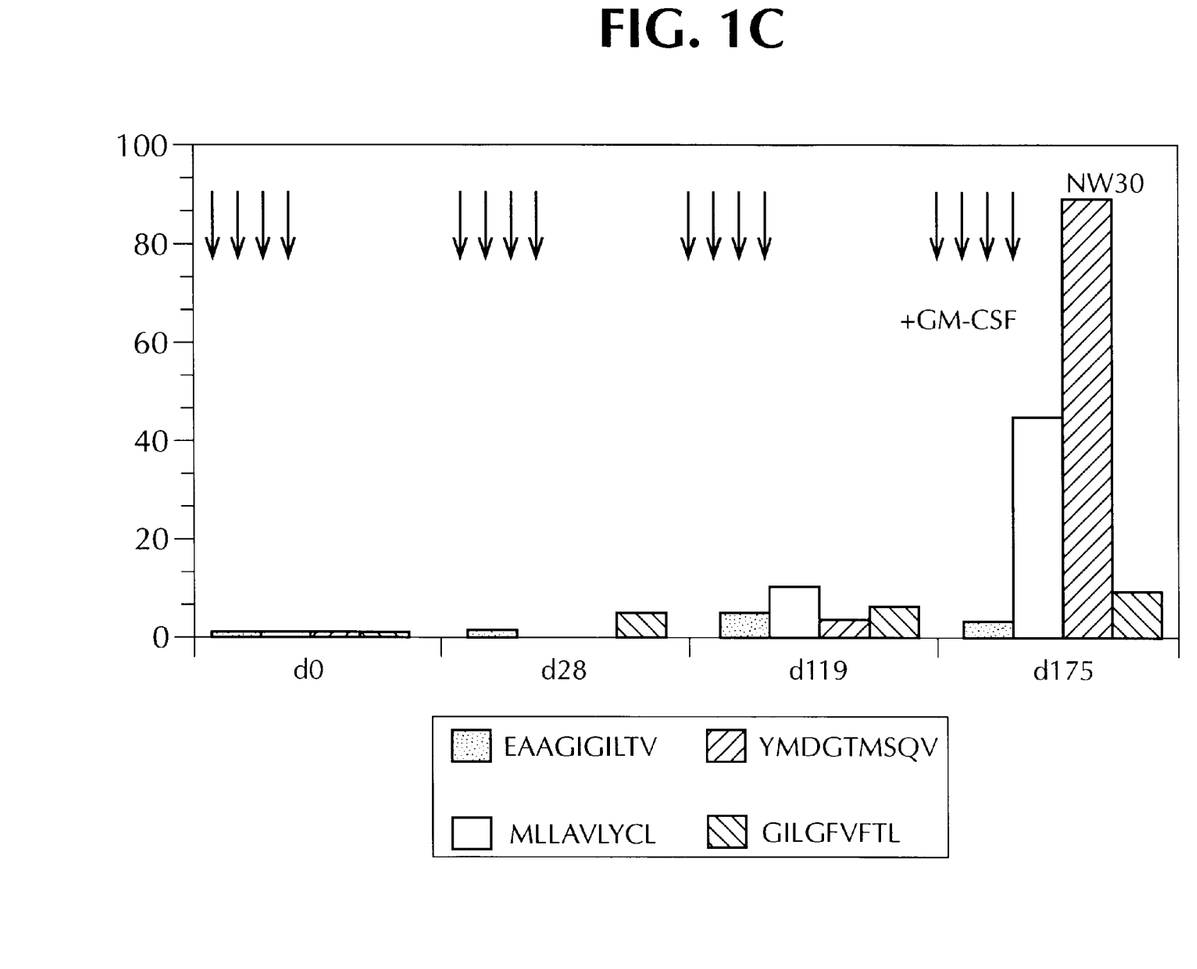

During the fourth cycle of peptide immunization, when GM-CSF was administered as an adjuvant, enhanced CTL reactivity was seen. All three subjects showed enhanced CTL activity against one peptide, one patient showed an increased response against another peptide, and a second patient exhibited enhanced activity against another peptide. These results are shown in FIGS. 1A, 1B and 1C.

TABLE 1

SCHEDULE FOR PATIENTS NW30, 33 AND 37

| DAY | WEEK | PEPTIDES INJECTED (SEQ ID NOS) | GM-CSF GIVEN | CTL ASSAY |
|---|---|---|---|---|
| 0 | 1 | 1,2,3,4,5 | — | Performed |
| 7 | 2 | 1,2,3,4,5 | — | |
| 14 | 3 | 1,2,3,4,5 | — | |
| 21 | 4 | 1,2,3,4,5 | — | |
| 28 | 5 | | — | Performed |
| 57 | 9 | 1,2,3,4,5 | — | |
| 77 | 12 | | — | Performed (Data not shown) |
| 85 | | | — | Performed |
| 98 | 15 | 1,2,3,4,5,6 | — | |
| 105 | 16 | 1,2,3,4,5,6 | — | |
| 112 | 17 | 1,2,3,4,5,6 | — | |
| 119 | 18 | 1,2,3,4,5,6 | — | Performed |
| 144 | 21 | | 75 $\mu$g | |
| 145 | 21 | | 75 $\mu$g | |
| 146 | 21 | | 75 $\mu$g | |
| 147 | 22 | 1,2,3,4,5,6 | 75 $\mu$g | |
| 148 | 22 | | 75 $\mu$g | |
| 149 | 22 | | 75 $\mu$g | |
| 150 | 22 | | | |
| 151 | 22 | | 75 $\mu$g | |
| 152 | 22 | | 75 $\mu$g | |
| 153 | 22 | | 75 $\mu$g | |
| 154 | 23 | 1,2,3,4,5,6 | 75 $\mu$g | |
| 155 | 23 | | 75 $\mu$g | |
| 156 | 23 | | 75 $\mu$g | |
| 157 | 23 | | — | |
| 158 | 23 | | 75 $\mu$g | |
| 159 | 23 | | 75 $\mu$g | |
| 160 | 23 | | 75 $\mu$g | |
| 161 | 24 | 1,2,3,4,5,6 | 75 $\mu$g | |
| 162 | 24 | | 75 $\mu$g | |
| 163 | 24 | | 75 $\mu$g | |
| 164 | 24 | | — | |
| 165 | 24 | | 75 $\mu$g | |
| 166 | 24 | | 75 $\mu$g | |
| 167 | 24 | | 75 $\mu$g | |
| 168 | 25 | 1,2,3,4,5,6 | 75 $\mu$g | |
| 169 | 25 | | 75 $\mu$g | |
| 170 | 25 | | 75 $\mu$g | |
| 171 | 25 | | — | |
| 172 | 25 | | — | |
| 173 | 25 | | — | |

TABLE 1-continued

SCHEDULE FOR PATIENTS NW30, 33 AND 37

| DAY | WEEK | PEPTIDES INJECTED (SEQ ID NOS) | GM-CSF GIVEN | CTL ASSAY |
|---|---|---|---|---|
| 174 | 25 | | — | |
| 175 | 26 | | — | Performed |

TABLE 2

SCHEDULE FOR PATIENTS NW28 AND NW29

| DAY | WEEK | PEPTIDES INJECTED (SEQ ID NOS) | GM-CSF GIVEN | CTL ASSAY |
|---|---|---|---|---|
| 0 | 1 | 1,2,3,4,5,6 | — | Performed |
| 7 | 2 | 1,2,3,4,5,6 | — | |
| 14 | 3 | 1,2,3,4,5,6 | — | |
| 21 | 4 | 1,2,3,4,5,6 | — | |
| 28 | | | — | Performed |
| 49 | 8 | 1,2,3,4,5,6 | — | Performed (Data not shown) |
| 56 | 9 | 1,2,3,4,5,6 | — | |
| 63 | 10 | 1,2,3,4,5,6 | — | |
| 70 | 11 | 1,2,3,4,5,6 | — | |
| 77 | 12 | | — | Performed (Data not shown) |
| 98 | 15 | 1,2,3,4,5,6 | — | |
| 105 | 16 | 1,2,3,4,5,6 | — | |
| 112 | 17 | 1,2,3,4,5,6 | — | |
| 119 | 18 | 1,2,3,4,5,6 | — | Performed |
| 144 | 21 | | 75 μg | |
| 145 | 21 | | 75 μg | |
| 146 | 21 | | 75 μg | |
| 147 | 22 | 1,2,3,4,5,6 | 75 μg | |
| 148 | 22 | | 75 μg | |
| 149 | 22 | | 75 μg | |
| 150 | 22 | | | |
| 151 | 22 | | 75 μg | |
| 152 | 22 | | 75 μg | |
| 153 | 22 | | 75 μg | |
| 154 | 23 | 1,2,3,4,5,6 | 75 μg | |
| 155 | 23 | | 75 μg | |
| 156 | 23 | | 75 μg | |
| 157 | | | — | |
| 158 | 23 | | 75 μg | |
| 159 | 23 | | 75 μg | |
| 160 | 23 | | 75 μg | |
| 161 | 24 | 1,2,3,4,5,6 | 75 μg | |
| 162 | 24 | | 75 μg | |
| 163 | 24 | | 75 μg | |
| 164 | 24 | | — | |
| 165 | 24 | | 75 μg | |
| 166 | 24 | | 75 μg | |
| 167 | 24 | | 75 μg | |
| 168 | 25 | 1,2,3,4,5,6 | 75 μg | |
| 169 | 25 | | 75 μg | |
| 170 | 25 | | 75 μg | |
| 171 | 25 | | — | |
| 172 | 25 | | — | |
| 173 | 25 | | — | |
| 174 | 25 | | — | |
| 175 | 26 | | — | Performed |

TABLE 3

DTH REACTIONS AFTER INTRADERMAL INOCULATION OF MELANOMA ASSOCIATED PEPTIDES

| | Melan A | | Tyrosinase | | gp100 | | flu |
|---|---|---|---|---|---|---|---|
| Patient NW28 | 1 AAGIGILTV | 2 EAAGIGILTV | 3 MLLAVLYCL | 4 YMDGTMSQV | 5 YLEPGPVTA | 6 LLDGTATLRL | 7 GILGPVFTL |
| peptide alone | − | − | (+) | − | − | − | (+) |
| peptide alone | − | − | (+) | − | − | − | (+) |
| +GM-CSF | − | − | ++ | (+) | − | − | + |
| NW29 | | | | | | | |
| peptide alone | − | − | (+) | − | − | − | (+) |
| peptide alone | − | − | (+) | − | − | − | (+) |
| +GM-CSF | − | (+) | ++ | + | − | − | ++ |
| NW30* | | | | | | | |
| peptide alone A | − | | | − | − | − | (+) |
| peptide alone B | − | | | − | − | − | (+) |
| peptide alone | | | (+) | − | − | − | (+) |
| +GM-CSF | | + | ++ | + | + | − | ++ |
| NW33* | | | | | | | |
| peptide alone A | − | | − | | − | − | + |
| peptide alone B | − | | − | | − | − | (+) |
| peptide alone | − | | (+) | | − | − | (+) |
| +GM-CSF | − | | ++ | | − | − | + |
| NW37* | | | | | | | |
| peptide alone A | − | | | − | − | − | (+) |
| peptide alone B | − | | | − | − | − | (+) |
| peptide alone | | (+) | (+) | − | − | − | + |
| +GM-CSF | | + | + | − | (+) | − | ++ |

Legend: * = enrolled in the LUD 95-001 protocol;
A = day 1–22;
B = day 57

EXAMPLE 5

All patients described in Examples 1–4 had progressing metastatic melanoma at the time of entering the study. Patient NW28 had unresectable lymph node metastases in the left supraclavicular region, infiltrating the skin. Using immunization with peptide alone, stabilization of the disease was documented by clinical examination and ultrasonography. Eight weeks after immunization with peptide plus GM-CSF, the tumor infiltration of the skin had disappeared and a partial regression of the measurable tumor mass was documented. Patient NW29 had multiple paraaortal and parailiacal lymph node metastases and a single liver metastasis. Using vaccination with peptide alone, minor regression of two paraaortal lesions was documented by CT scan while the other lesions remained stable. Eight weeks after immunization with peptide plus GM-CSF, the liver metastasis had completely regressed. Two of the paraaortal lymph nodes and one parailiacal lymph node showed a partial regression as assessed by CT scan. No new metastatic lesions were detected. Patient NW30 had a growing local recurrence in his left thigh, that had been resected before three times at monthly intervals. At the time of the first immunization, the tumor was 1.2 cm in diameter. Eight weeks after the start of immunization with peptide alone, no further growth of the tumor was detected. Eight weeks after vaccination with peptide plus GM-CSF, the tumor mass had completely regressed. No new metastatic lesions were detected.

The examples supra, show that GM-CSF functions as an adjuvant in that it enhanced or provoked the response of T cells to molecules which, theoretically, should bind to MHC molecules on the surface of cells, and thereby provoke proliferation of cytolytic T cells against these complexes of molecules. The DTH reaction studies presented herein clearly show this. The in vivo efficacy should be taken as evidence that the same type of reaction would take place in vitro, because the principles underlying the response are the same. Similarly, the known immune response of the described and tested peptides is a T cell response; however, there is no reason to doubt that an equivalent B cell response could also be provoked or enhanced, with an appropriate molecule.

The immunogens of this invention are preferably, but not necessarily TRAPs, TRAs, and combinations of these, meaning that they do not include haptens, carriers, precipitated alum, or any of the materials normally associated with materials which are or are expected to be poorly immunogenic. In especially preferred embodiments, the compositions consist essentially of the immunogen and the adjuvant.

The amount of immunogen, e.g., TRAP or TRA used will vary, depending upon the purpose of the immunization and the subject to which it is administered. For example, in the case of generating murine antibodies which can then be used, e.g., to diagnose for the presence of cancer cells presenting a TRA, the amount of protein or peptide may be less than that used in a course of in vivo therapy, such as that described in the example, supra. In general, a preferred dose can range from about 1 ug to about 750 ug of protein or peptide per dose. In a preferred embodiment, the range is from about 10 ug to about 500 ug. Most preferably, anywhere from about 30 ug to about 300 ug per dose may be used. Of course, in the context of the therapeutic aspect of the invention, the investigator will modify the dose, as a six month old infant will require dosing different from a full grown man, e.g. The mode of administration may vary, with preferred forms being oral, subcutaneous, intramuscular, intravenous and intraperitoneal administration.

The choice of immunogen, e.g., TRAP or TRA protein or peptide in the composition will depend upon parameters determinable by the artisan. It is art recognized, for example, that different TRAs are presented by the various MHC molecules. As such, if a subject is typed, using well known techniques, as presenting HLA-A2 molecules on the surface of tumor cells, one will use a TRA presented by HLA-A2 molecules rather than one presented by, e.g., HLA-Cw* 1601, HLA-A1, HLA-B24, HLA-B8, HLA-B44, HLA-Cw6, etc. All of these MHC molecules are known to present tumor rejection antigens. Similarly, using techniques such as polymerase chain reaction ("PCR"), lysis studies, and other assay methodologies which are well known in the art, one can determine which tumor rejection antigen precursor gene or genes are being expressed by a subject patient. This will lead to the decision as to what protein or peptide to use. Again, by way of example, if a subject's tumor cells are expressing MAGE-3 but not MAGE-1, the peptide used in immunization should be derived from MAGE-3, and not MAGE-1.

Thus, the compositions of the invention include an immunogen and GM-CSF, wherein said GM-CSF is present in an adjuvant effective amount. The two components may be combined, or may be presented in separate portions as part of a kit, e.g. The specific peptides of SEQ ID NOS: 1, 2, 3, 5 and 6 are preferred as immunogens, but any immunogen, such as the various TRAs described herein, are include within the ambit of the invention.

Also a part of the invention is a method for provoking an immune response in a subject. The method comprises administering GM-CSF to a subject, followed by administration of the immunogenic material. Optionally, but not necessarily, the immunogen may be administered to the subject prior to the administration of the GM-CSF.

While the examples show that vaccinations with peptides and GM-CSF provoked both DTH and immunological reactions, it will be understood by the skilled artisan that the use of GM-CSF as an adjuvant clearly is a part of this invention. It is well known that various pathological conditions, such as cancer (e.g., melanoma), are characterized by the presentation of CTL epitopes are formed by interaction of MHC molecule and peptides which specifically bind to them. Thus, one aspect of the invention is the provocation, or enhancement, of an immune response by administering to the individual an amount of GM-CSF sufficient to provoke or enhance an immune response to the subject. The individuals so treated will be subjects who show characteristics linked to the pathological conditions referred to surra, such as the presentation of complexes of MHC and peptides on cell surfaces, which then act as epitopes or targets for cytolytic T cells. Other types of immune response, such as B cell responses, will be clear to the skilled artisan, and need not be elaborated upon herein.

The time interval between administrations may vary, but is preferably from about two days to about two weeks, most preferably two days to one week (i.e., seven days). Thus, a given protocol may begin, at day 1, with administration of an immunogen, followed by administration of GM-CSF at day 3, and further administration of additional immunogen at day 5. These patterns of immunization may be repeated, e.g., from 2 to 10 times, most preferably from 2 to 4 times, with periods wherein no immunogen or GM-CSF are administered to follow, with the pause followed by repeated immunizations. Again, these periods of immunization and pause may be repeated in a given protocol.

The amounts of immunogen and GM-CSF used may vary, depending upon the particular application; however, a single dose of immunogen is preferably anywhere from about 10 ug up to about 5000 ug, more preferably from about 50 ug to about 2500 ug, most preferably about 100 ug to about 1000 ug. For GM-CSF, a dose of 10 ug to about 100 ug per dose is preferred. Modes of administration possible include intradermal, subcutaneous, and intravenous administration, implantation in the form of a time release formulation, etc. Any and all forms of administration known to the art are encompassed herein.

While the preferred molecules discussed herein are referred to as "tumor" rejection antigens and "tumor" rejection antigen precursors, it is intended that their use, in a therapeutic and also a diagnostic context, extends beyond cancer per se. The art is familiar with pathological conditions, such as diaplastic nevis, which are not cancer per se, but where the cells of the afflicted individuals are in fact characterized by transformation. Any and all such conditions are within the intended ambit of the invention.

Other aspects of the invention will be clear to the skilled artisan and need not be reiterated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. An immunogenic composition consisting of:
   (a) at least one peptide molecule, said at least one peptide molecule consisting of an amino acid sequence for a tumor rejection antigen, where said peptide molecule binds to an MHC molecule on a cell surface to provide a peptide—MHC complex; and
   (b) an amount of granulocyte macrophage colony stimulation factor sufficient to stimulate an antigen specific, $CD8^+$ cytolytic T cell response against said peptide—MHC complex.

2. The immunogenic composition of claim 1 wherein said peptide is selected from the group consisting of SEQ ID NO: 1, SEQ ID NO: 2, SEQ ID NO: 3, SEQ ID NO: 4, SEQ ID NO: 5, and SEQ ID NO: 6.

3. The immunogenic composition of claim 1, wherein said MHC molecule is HLA-A2.

4. A method for generating an antigen specific, $CD8^+$ cytolytic T cell response in a patient in need of an antigen specific, $CD8^+$ cytolytic T cell response comprising administering separately to said patient:
   (a) at least one peptide molecule consisting of an amino acid sequence for a tumor rejection antigen, wherein said peptide molecule binds to an MHC molecule on a cell surface to provide a peptide—MHC complex; and
   (b) an amount of granulocyte macrophage colony stimulating factor (GM-CSF) sufficient to stimulate an antigen specific, $CD8^+$ cytolytic T cell response directed against said peptide—MHC complex.

5. The method of claim 4 comprising administering said GM-CSF of (b) following administering said peptide of (a).

6. The method of claim 5 comprising administering said peptide of (a) from about 2 days to about 2 weeks prior to administering said GM-CSF of (b).

7. The method of claim 4 comprising administering said peptide molecule of (a) following administering said GM-CSF of (b).

8. The method of claim 5, further comprising administering to said patient an additional amount of the at least one peptide molecule of (a) following administering said GM-CSF of (b).

9. The method of claim 8, comprising administering said additional peptide from about 2 days to about two weeks following administration of said GM-CSF of (b).

10. The method of claim 4 wherein said peptide molecule of (a) is administered in an amount ranging from about 10 ug to about 1000 ug per dose.

11. The method of claim 8 wherein said additional peptide molecule is administered in an amount ranging from about 10 ug to about 1000 ug per dose.

12. The method of claim 4, comprising administering said GM-CSF of (b) in an amount ranging from about 10 ug to about 5000 ug per dose.

13. The method of claim 12, comprising administering said GM-CSF in an amount ranging from about 10 ug to about 100 ug per dose.

14. A kit useful for generating an antigen specific, $CD8^+$ cytolytic T cell response against a tumor rejection antigen, consisting of separate portions of:
   (a) at least one peptide molecule consisting of an amino acid sequence for a tumor rejection antigen (TRA), where said peptide molecule binds to an MHC molecule on a cell surface to provide a peptide—MHC complex; and
   (b) an amount of granulocyte macrophage colony stimulation factor sufficient to stimulate an antigen specific, $CD8^+$ cytolytic T cell response directed against said peptide—MHC complex.

15. A method for treating a cancer in a patient in need of an antigen specific, $CD8^+$ cytolytic T cell response, comprising administering to said patient in sequential order:
   (a) at least one peptide selected from the group consisting of SEQ ID NO: 1, SEQ ID NO: 2, SEQ ID NO: 3, SEQ ID NO: 4, SEQ ID NO: 5, and SEQ ID NO: 6, where said peptide is presented by an MHC molecule on a cancer cell surface to provide a peptide—MHC complex;
   (b) an amount of GM-CSF sufficient for stimulation of an antigen specific, $CD8^+$ cytolytic T cell response to said peptide of said peptide—MHC complex, followed by
   (c) an additional amount of the at least one peptide of step (a).

16. A method of generating an antigen specific, $CD8^+$ cytolytic T cell response, in a patient in need of of an antigen specific, $CD8^+$, cytolytic T cell response comprising administering to said patient in sequential order;
   (a) at least one peptide selected from the group consisting of SEQ ID NO: 1, SEQ ID NO: 2, SFQ ID NO: 3, SEQ ID NO: 4, SEQ ID NO: 5, and SEQ ID NO:6;

(b) an amount of GM-CSF sufficient for stimulating an antigen specific, CD8$^+$ cytolytic T cell response to said peptide of (a);

(c) an additional amount of at least one peptide of step (a); and (d) an additional amount of GM-CSF sufficient for stimulating an antigen specific, CD8$^+$ cytolytic T cell response to said peptide of (c).

17. A method for generating an antigen specific, CD8$^+$ cytolytic T cell response to a patient in need of an antigen specific, CD8$^+$ cytolytic T cell response, wherein said patient has a known HLA type, comprising administering to said patient, in sequential order:

(a) one of (i) a tumor rejection antigen (TRA) or (ii) a tumor rejection antigen precursor (TRAP) wherein said TRAP is processed in vivo to a TRA, which binds to said HLA; and (iii) an amount of GM-CSF effective for stimulating a first, antigen specific CD8$^+$ cytolytic T cell response to said TRA; followed by (b) an additional amount of said TRA of (a)(i) or TRAP of (a)(ii); and (c) an additional amount of GM-CSF effective for stimulating a second, antigen specific CD8$^+$ cytolytic T cell response to said TRA.

18. A method for generating an antigen specific, CD8$^+$ cytolytic T cell response in a patient in need of an antigen specific, CD8$^+$ cytolytic T cell response, comprising administering to said patient in sequential order:

(a)(i) a material selected from the group consisting of a TRA and a TRAP which is processed in vivo by said patient to said TRA; and (ii) an amount of GM-CSF effective for stimulating a first, antigen specific, CD8$^+$ cytolytic T cell response to said TRA;

(b) an additional amount of the material of (a)(i); and (c) an additional amount of GM-CSF effective for stimulating a second, antigen specific CD8$^+$ cytolytic T cell response to said TRA.

* * * * *

```
                          SEQUENCE LISTING (1) GENERAL INFORMATION:

(iii) NUMBER OF SEQUENCES:  6

(2) INFORMATION FOR SEQ ID NO: 1:

(i) SEQUENCE CHARACTERISTICS:
        (A) LENGTH:  9 amino acids
        (B) TYPE:  amino acid
        (D) TOPOLOGY:  linear (xi) SEQUENCE DESCRIPTION:  SEQ ID NO: 1:

Tyr Met Asp Gly Thr Met Ser Gln Val
                 5

(2) INFORMATION FOR SEQ ID NO: 2:

(i) SEQUENCE CHARACTERISTICS:
        (A) LENGTH:  10 amino acids
        (B) TYPE:  amino acid
        (D) TOPOLOGY:  linear (xi) SEQUENCE DESCRIPTION:  SEQ ID NO: 2:

Glu Ala Ala Gly Ile Gly Ile Leu Thr Val
                 5                  10

(2) INFORMATION FOR SEQ ID NO: 3:

(i) SEQUENCE CHARACTERISTICS:
        (A) LENGTH:  9 amino acids
        (B) TYPE:  amino acid
        (D) TOPOLOGY:  linear (xi) SEQUENCE DESCRIPTION:  SEQ ID NO: 3:

Tyr Leu Glu Pro Gly Pro Val Thr Ala
                 5

(2) INFORMATION FOR SEQ ID NO: 4:

(i) SEQUENCE CHARACTERISTICS:
        (A) LENGTH:  10 amino acids
        (B) TYPE:  amino acid
        (D) TOPOLOGY:  linear (xi) SEQUENCE DESCRIPTION:  SEQ ID NO: 4:

Leu Leu Asp Gly Thr Ala Thr Leu Arg Leu
                 5                  10
```

-continued (2) INFORMATION FOR SEQ ID NO: 5:

(i) SEQUENCE CHARACTERISTICS:
        (A) LENGTH: 9 amino acids
        (B) TYPE: amino acid
        (D) TOPOLOGY: linear     (xi) SEQUENCE DESCRIPTION: SEQ ID NO: 5:

Gly Ile Leu Gly Phe Val Phe Thr Leu
                   5

(2) INFORMATION FOR SEQ ID NO: 6:

(i) SEQUENCE CHARACTERISTICS:
        (A) LENGTH: 9 amino acids
        (B) TYPE: amino acid
        (D) TOPOLOGY: linear     (xi) SEQUENCE DESCRIPTION: SEQ ID NO: 6:

Met Leu Leu Ala Val Leu Tyr Cys Leu